United States Patent [19]

Transue et al.

[11] Patent Number: 4,799,481
[45] Date of Patent: Jan. 24, 1989

[54] SURGICAL HEMOSTATIC CLIPS

[75] Inventors: James A. Transue, Somerville; John N. Pynn, Whitehouse Station; Joseph Innocencio, Kenilworth; Michael S. Thomas, Somerset; Arthur A. Gertzman, Bridgewater, all of N.J.

[73] Assignee: Ethicon, Inc., Somerville, N.J.

[21] Appl. No.: 36,037

[22] Filed: Apr. 8, 1987

[51] Int. Cl.$^4$ .............................................. A61B 17/12
[52] U.S. Cl. .................................... 128/325; 128/346; 227/DIG. 1
[58] Field of Search ............... 128/325, 326, 337, 346; 227/DIG. 1

[56] References Cited

U.S. PATENT DOCUMENTS

| 3,270,745 | 9/1966 | Wood | 128/325 |
| 3,363,628 | 1/1968 | Wood | 128/325 |
| 4,505,274 | 3/1985 | Speelman | 128/337 |
| 4,590,937 | 5/1986 | Deniega | 128/325 |
| 4,702,247 | 10/1987 | Blake | 128/325 |

Primary Examiner—Michael H. Thaler

[57] ABSTRACT

A hemostatic clip for surgical use is disclosed having grooves on the inner surfaces of the legs which form an asterisk type pattern upon closure, knee bends in each leg which are opposed by notches or grooves that enhance the ability of the legs to fully straighten upon closure, and distal flat surfaces on the ends of the clip legs to prevent scissoring and ensure hemostasis when the clip is closed.

3 Claims, 3 Drawing Sheets

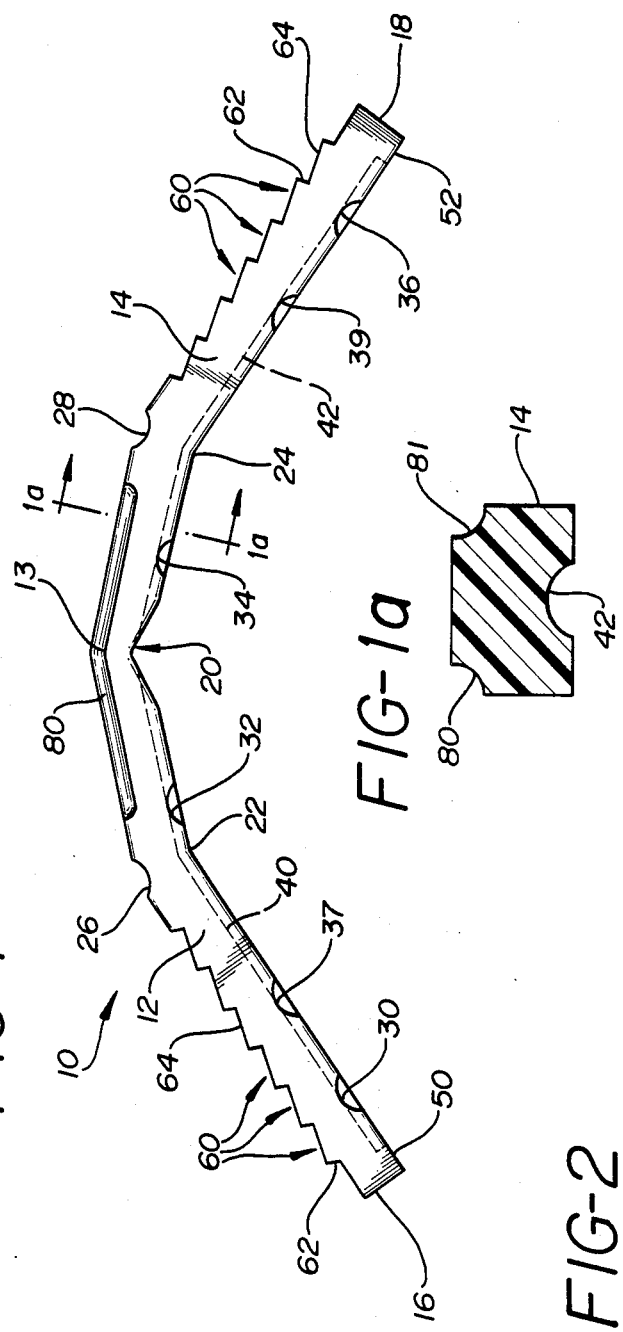
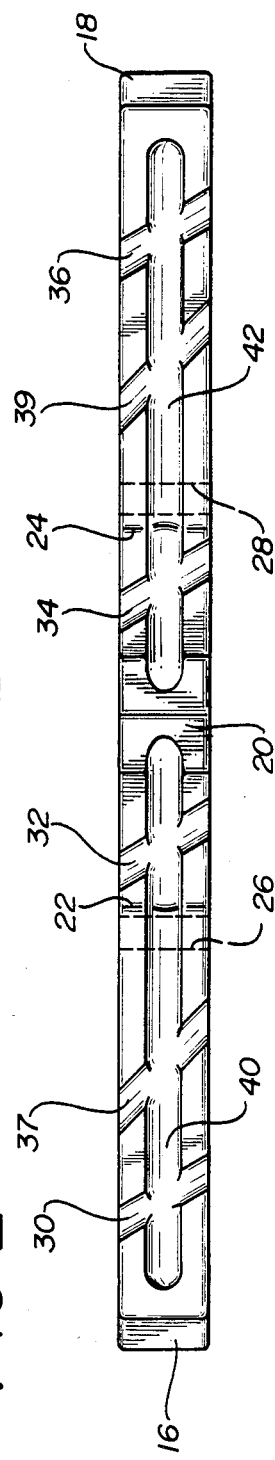

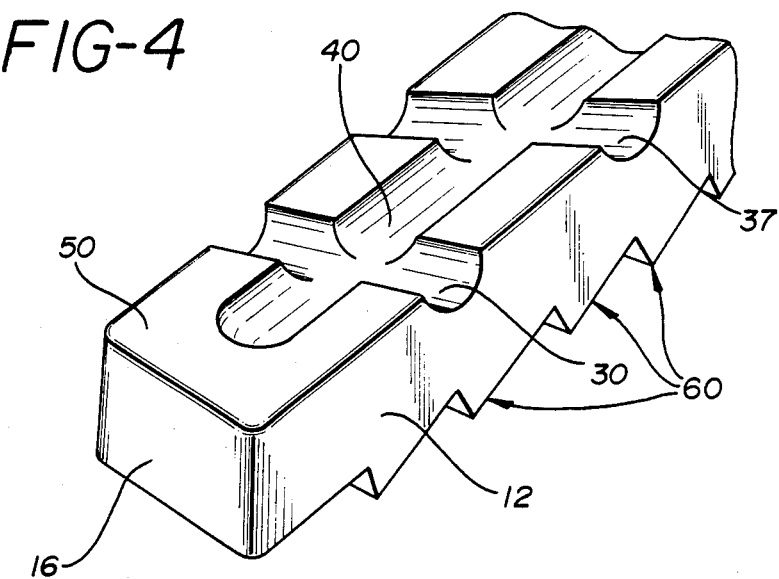
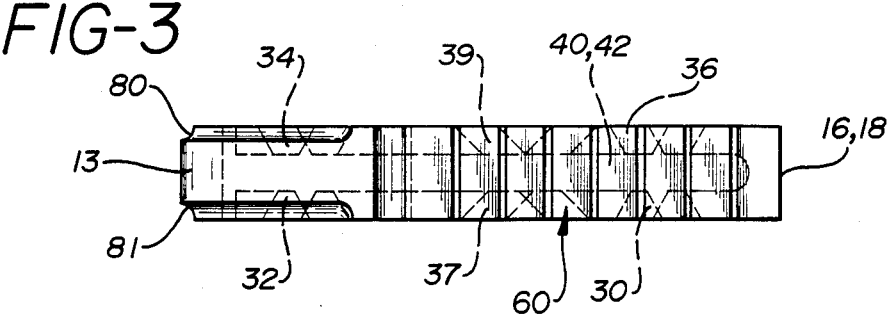
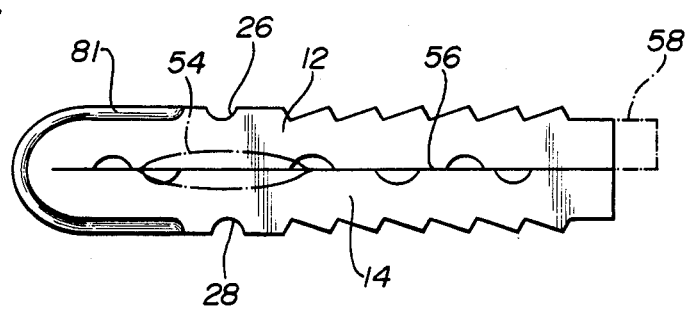

SURGICAL HEMOSTATIC CLIPS

This invention relates to devices used to close or shut tubular members and, more particularly, to metallic hemostatic clips used to close blood vessels within the body.

During many surgical procedures, the surgeon will have to close or ligate various blood vessels before severing the vessels in order to prevent excessive bleeding and reduce the risk to the patient of blood loss. One technique to close a blood vessel is to ligate it; that is, tie a surgical suture about the vessel to close the vessel. Also, there are various types of metal devices or clips having a pair of legs connected at their proximal ends that can be placed about the vessel and the legs urged or squeezed together to shut the blood vessel. Hemostatic clips are well known in the prior art and are disclosed in numerous U.S. patents as, for example, U.S. Pat. Nos. 3,439,523; 3,270,745; 3,363,628; 3,463,156; 3,439,522; 3,439,523; 4,146,130; and 4,449,530.

A serious problem with the prior art hemostatic clips is, though they may be closed about a blood vessel and shut off the flow of blood, there is very often a gap left between the legs of the closed clip. In a typical surgical procedure, the open distal ends of the clip are placed about the vessel to be closed and, using a suitable instrument, the legs are urged together in an attempt to bring the distal ends in contact and place the legs substantially parallel and in uniform contact with the surface of the vessel. However, in practice the uniform contact is very seldom attained and instead there are spaces between the legs, or areas of the leg of the clip which are in greater contact with the vessel than other areas of the clip. The spaces or areas with the lesser contact or pressure on the vessel are termed the gap. This gap very often allows the clip to move or slide along the length of the vessel about which it has been closed. When this happens, and the vessel has been cut, in many instances, the clip will slide off the cut end of the blood vessel thus allowing the flow of blood from the now unclosed vessel. The gap in part is caused by the construction of the clip in that the clip is designed so that the distal end of the leg members close first to entrap the vessel in the clip and prevent the vessel from slipping out of the clip on closing the leg members. The leg members are then urged toward each other to close the vessel. The gap is also in part a function of the yield strength of the metal used to form the clip. The higher the yield strength of the metal, the less malleable it is and therefore the greater the possibility of forming a gap and the greater the size of the formed gap upon closing the clip.

While the gap is generally not of sufficient size to allow leakage of blood at the time it is applied and the vessel severed, as mentioned above, the gap is often sufficient to allow the clip to slide along the blood vessel. This can often happen when the surgeon or nurse in the surgical area is attempting to wipe blood or clean the operative area with a sponge, and a corner of the sponge catches on the clip. If the gap is large enough the clip will slide on the vessel even to the point of being removed from the cut end of the vessel.

One prior art technique for alleviating the gapping problem is to produce the hemostatic clip with a thinned hinge area at the point of connection of the proximal ends of the clip legs. Such a clip is described in U.S. Pat. No. 4,449,530. The clip of that patent will readily close about a blood vessel, leaving substantially no gap between the legs in the closed position. In one embodiment of that invention, a clip is illustrated having a single bend at the hinged area of the clip. In another embodiment, a clip is shown with two further bends one at a point on each leg intermediate the hinged proximal and distal ends of each leg. The purpose of the thrice-bent configuration to entrap the vessel in the vicinity of the intermediate leg bends as the distal ends are closed toward each other. As the clip is further compressed to its fully closed condition, it is intended that the intermediate leg bends be eliminated leaving the legs in a substantially parallel alignment. Such, however, is often not the case, as some gap or lesser contact pressure may remain in the intermediate bend region of the clip legs.

In accordance with the principles of the present invention, a metallic hemostatic clip is provided which substantially alleviates the gapping or uneven closure pressure problem of prior art clips. On the outer, applier contacting side of the clip, and in the vicinity of the intermediate bend in the legs of the clip, a notch or depression is provided in the surface of the clip. As the two legs of the hemostatic clip are compressed toward each other, the notch or depression in the outer surface of the legs will promote a tendency for each leg to unbend to a fully straightened condition whereby the closed legs will be parallel and excessive gapping and uneven vessel contact is substantially eliminated. Such a tendency is surprisingly promoted without diminishing the opening strength of the clip.

Various techniques have been employed in the prior art to impede the tendency of a closed clip to slide along the length of a vessel about which it has been closed. In the aforementioned U.S. Pat. No. 4,449,530, the opposing inner surfaces of the clip legs are embossed or scored with a diamond type pattern. In U.S. Pat. No. 4,188,953, the inner surface of each leg is scored with parallel grooves oriented at an angle with respect to the longitudinal length of the leg. The orientation of the groove pattern is such that when the two legs are folded together the grooves superimpose in a cross-hatched pattern.

In accordance with another aspect of the present invention, a hemostatic clip contains a plurality of grooves on the inner surface of each leg which are angularly disposed with respect to the longitudinal axis of each leg. Extending parallel to the longitudinal axis of each leg and intersecting the angularly disposed grooves is a longitudinal groove. The superimposition of these groove patterns when the clip is closed forms an asterisk type pattern. It has been found that this pattern enhances retention of the closed clip both axially and longitudinally on the vessel.

It has further been found to be desirable to terminate each longitudinal groove prior to reaching the distal end of the leg. Such a termination leaves a distal flat region on the inner surface of each leg end. In clips of the prior art, such as those shown in U.S. Pat. No. 3,270,745, central channels in the two legs extend to the ends of the legs. The legs of such clips will tend to "scissor", or skew to an offset orientation when the clip is closed. The scissoring action of the two legs, instead of closing the vessel, will pinch or sever the vessel by concentrating forces along a line of pressure, leading to extensive bleeding instead of vessel closure. This problem is overcome by incorporating distal flat surfaces on the inner, vessel contacting surfaces of the leg ends.

In the drawings:

FIG. 1 illustrates a side view of a hemostatic clip constructed in accordance with the principles of the present invention;

FIG. 1a is a cross-sectional view taken in the vicinity of the hinge of the hinge of the clip of FIG. 1;

FIG. 2 is a plan view of the inner, vessel contacting surface of a hemostatic clip of the present invention in a flat, open condition;

FIG. 3 is a plan view of the hemostatic clip of FIG. 2 in a closed condition;

FIG. 4 is an elevational view of the distal end of a hemostatic clip of the present invention;

FIG. 5 is a side view of a clip of the present invention in a closed condition;

Figure 6:
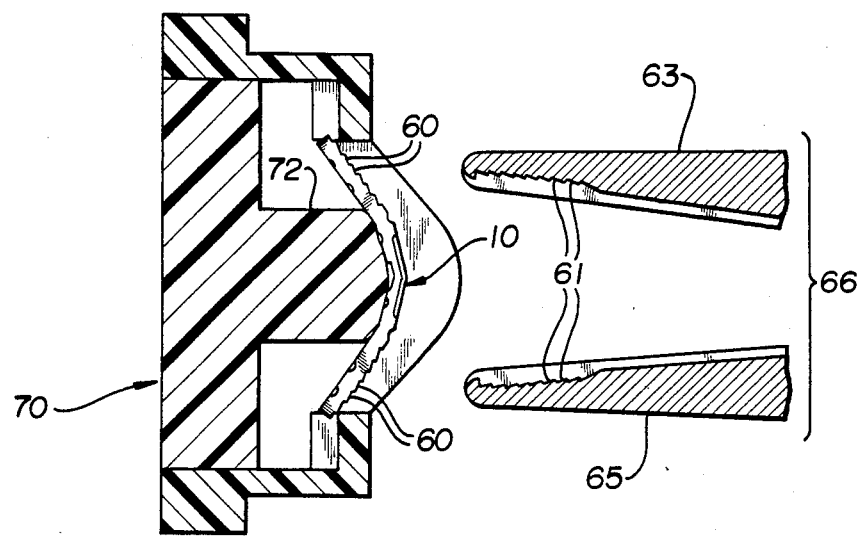
FIG. 6 is a partially cross-sectional view of a hemostatic clip of the present invention in a clip cartridge.

Referring to FIG. 1, a hemostatic clip 10 constructed in accordance with the principles of the present invention is shown. The clip 10 may be made of any of the conventional variety of surgical metals which can be sterilized and are nontoxic and can therefore be tolerated within the body for indefinite periods of time. Suitable materials with these characteristics include stainless steel titanium and tantalum. The clip may be conveniently formed from wire of these materials into the shape illustrated in the FIGURE. When produced in the angular shape shown in the drawing, the clip may be conveniently stored prior to use in a cartridge, to be described subsequently.

The clip 10 comprises two legs 12 and 14, which are jointed at their proximal ends at 13. The legs also have distal ends 16 and 18. A hinge recess 20 is located in the tissue side of the clip at the jointure 13 of the proximal ends of the legs. The hinge recess 20 provides relief at the hinge point of the clip where the clip is intended to bend as it is closed about a vessel. The angularly inclined shape of the recess compels the clip to bend at the precise jointure 13, which prevents overlapping of the distal ends of the clip at closure.

Located on the applier contacting longitudinal edges of the clip and opposite the hinge recess 20 are two recessed fillets 80 and 81, shown more clearly in FIG. 1a. The purpose of these fillets is two-fold. First, the removal of metal in the formation of the fillets leaves voids at the two outer corners of the clip opposite the hinge recess. As the clip is subsequently bent at the hinge recess during closure, the fillets act to relieve tensile stresses that would otherwise concentrate in these corners. Full closure is thus more easily achieved, with virtually no gap between the clip legs.

Second, the presence of the fillets 80 and 81 allow a reorientation of the cross-sectional properties of the generally rectangular hinge portion of the clip. In the cross-section of the clip at the hinge approximately the inner one-third of the metal is under compression during bending. The outer two-thirds of the metal at the hinge is under the force of tension. The two force regions are separated by an imaginary line known as the neutral axis. The two fillets, which displace metal that would otherwise be under a tensile force, brings the two force regions more nearly into equilibrium. This decreases the force required to close the clip, and when the clip is fully closed, any tendency of the clip to reopen from its gapless condition is not increased.

Each leg 12, 14 has a bend located at a point 22, 24, on the tissue contacting surface intermediate its distal and proximal ends. Located on the applier side of each leg at each bend point 22, 24 is a notch 26, 28. Each notch comprises a shallow depression extending transversely across the outer, applier contacting surface of the leg at the bend point. The notches promote a tendency for each leg to fully straighten at the bend point at closure, thereby minimizing residual gapping between the closed clip legs. As the metallic clip is closed by an applier, it initially bends only at the hinge recess 20, until the distal leg ends contact each other. Thereafter the knee bends begin to straighten. As they do so, two forces come into play in the metal of the bends. tension and compression. The metal on the inner portion of a cross-section of the leg at the bend undergoes tension as the leg straightens. The outer portion of the leg metal experiences forces of compression. The areas of these two forces within the metal of the bend are separated by a "neutral axis" which is located generally parallel to the tissue contacting surface of the bend and one-third of the distance up from the tissue contacting surface to the nominal applier contacting surface. It is thus seen that more metal is subject to the compressive force than the force of tension. The notch acts as a relief into which the material undergoing compression can expand. As the leg closes, the metal on either side of the notch is compressed toward the notch and occupies a portion of its original volume. The clip will remain closed under the tensile force of the metal of the clip. without gapping. Preferably the depression of the notch extends no further than halfway through the knee bend from the nominal applier surface of the leg, and most preferably no further than one-third of the nominal leg thickness. By promoting full straightening of the legs, the security of the closed clip on the vessel is enhanced and improved hemostasis results.

Also located on the applier side of each leg and toward the distal ends 16 18 are a number of saw tooth shaped serrations 60. These serrations engage with complementing serrations or grooves in the applier tips, and serve two functions. After a clip has been gripped by an applier and partially closed to a barn-like shape in a clip cartridge, the smaller, riser like surfaces 62 of the serrations provide interposing surfaces against which the applier can press when pulling the clip from the cartridge. The riser like surfaces 62 thus prevent forward clip movement in the applier. When the applier held clip then probes into tissue or over a vessel the angled step like surfaces 64 of the serrations provide interposing surfaces against which the applier will press to hold the clip in place in the forward end of the applier. The angled surfaces thus enhance rearward clip retention during clip placement.

Located on the tissue contacting surface of the clip legs are a plurality of angled transverse grooves 30–39. Extending longitudinally along the tissue side of the clip legs, and intersecting the transverse grooves, are two central grooves 40 and 42. The grooves are clearly illustrated in the plan view of the tissue side of the clip in FIG. 2. These grooves are configured to cooperatively provide a pattern that will grip the tissue of a vessel and provide reliable hemostasis and resistance to dislodging of the closed clip. The central grooves 40, 42 cooperate with the transverse grooves 30–39 to form an "asterisk" pattern of overlapping grooves when the clip is closed, as shown in FIG. 3. This asterisk pattern of dentition upon closure of the clip provides improved security of the clip both axially and longitudinally on the vessel which will maintain hemostasis.

It has been found that the clips of the present invention provide such a high degree of on-vessel security that the surgical procedure is simplified. Because of concern with the tendency of prior art clips to slide off the end of a severed vessel when a sponge is wiped over the surgical area, it has been common practice for surgeons to cut a ligated vessel a short distance from the clip. This will leave uncompressed vessel tissue on either side of the portion of the vessel which is flattened by the clip. In particular, the short portion of uncompressed vessel or cuff, at the cut end will provide resistance to the clip when a wiping sponge urges the clip toward the cut end of the vessel. Thus, the cuff helps to prevent the clip from sliding off of the vessel when urged to do so by a sponge.

However, in order to leave the desired cuff, it is necessary for the surgeon to cut the vessel with extreme care, spacing the cutting instrument an exact distance from the hemostasis, so as to leave only a precisely determined length of vessel adjacent the clip. Since the hemostasis will close off all nourishment to the portion of the vessel compressed by the clip and to the cuff, these portions of the vessel will eventually necrose and possibly create a condition of sepsis and adhesions within the body. Since it is desirable to create as little scar tissue as possible following a surgical procedure, the surgeon must cut the vessel precisely so as to leave only sufficient vessel tissue to maintain on-vessel security, without leaving excess tissue that will become scar tissue.

In tests with clips of the present invention with their asterisk pattern of grooves, the vessels subject to hemostasis have been cut flush with the side of the clip itself. Although this procedure leaves no vessel cuff to provide on-vessel security, the clips of the present invention have been found to hold so securely in place that they are not easily dislodged by a wiping sponge. This cutting procedure is simple for the surgeon, who does not have to precisely gauge the distance between the clip and the point of the cut. Instead, the surgeon can conveniently use the side of the clip as a guide for the cutting instrument. Of course, cutting the vessel flush with the clip will leave a minimal amount of scar tissue at the ligated site post-operatively.

In the elevational view of FIG. 4 of the distal end of a clip leg, it may be seen that it is preferred that the central grooves 40, 42 terminate before reaching the most distal ends of the clip. This maintains a distal flat surface 50, 52 on the tissue side of the distal end of the clip. These distal flat surfaces conveniently provide flush surfaces for closure of the opposing clip legs against each other. The employment of distal flat surfaces impedes any tendency of the clip legs to "scissor" as the clip is compressed to its fully closed condition, and additionally acts to seal off any flow through the central, longitudinal grooves. When the distal end surfaces are not flat, the clip ends can readily slide laterally to a position of misalignment. Upon continued closure of the clips the misaligned legs, by virtue of a concentrated line of force, will act as the blades of a scissors and, instead of compressively closing the vessel, the clip legs could sever the vessel. The employment of the distal flat surfaces retards the possibility of such an occurrence.

In a constructed embodiment of the present invention, the grooves 40, 42 were terminated at a location leaving a distal flat surface dimension between the groove termination and the end of the clip which was approximately half the dimension of the width of the distal flat across the distal end of the clip.

FIG. 5 is a side view of a hemostatic clip of the present invention in a closed condition. The central line 56 represents the idealized line of contact of the clip legs 12, 14 with perfect gapless closure. The dotted area 54 between the knee notches 26, 28 represents the gapping that would be present were it not for the presence of the knee notches. The dashed area 58 represents the overlap of the distal ends of the clip legs that is prevented by use of the tapered hinge recess. The focusing hinge recess compels the clip to close With its distal leg ends in longitudinal alignment.

FIG. 6 illustrates a hemostatic clip 10 of the present invention in a clip cartridge 70, which may hold a number of such clips. The cartridge 70 is more fully described in U.S. Pat. No. 3,713,533. In the cartridge the clip is suspended in a shape as shown in FIG. 1, with its distal leg ends contacting opposite shoulders of the cartridge, and the central portion of the clip contacting a central projection or rail 72. The cartridge 70 and clip 10 are shown being approached by the tips 62 and 64 of an applier instrument 66. Located on the inner surfaces of the applier tips are a plurality of serrations 61, which are designed to mate with the serrations 60 on the clip 10. As the applier tips contact the legs of the clip in the cartridge, they begin to bend the clip at the hinge 20. The clip is bent around the rail 72 into a barn-like shape, and the clip serrations 60 engage with the serrations 61 in the applier tips. The bent clip is then withdrawn from the cartridge, aided by the engagement of the serrations.

Figure 7:
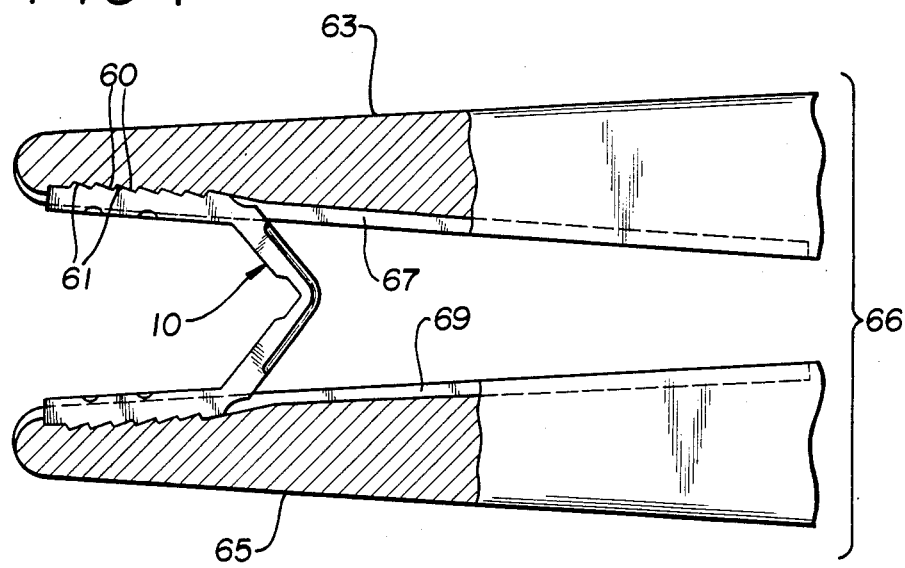
FIG. 7 is a partially cross-sectional view of a hemostatic clip of the present invention being held by a clip applier instrument.

The withdrawn clip is held in the applier tips as shown in FIG. 7. Lateral movement of the clip 10 within the applier tips is prevented by channel sidewalls 67 and 69 in the inner surfaces of the tips, which are just slightly wider than the lateral dimension of the clip. Forward and rearward movement of the clip are retarded by the engagement of the serrations 60 and 61.

What is claimed is:

1. A metallic surgical hemostatic clip comprising first and second legs each exhibiting a major longitudinal dimension and each having a tissue contacting surface and an applier contacting surface, said legs being joined at their proximate ends at a hinge region of the clip, said legs each exhibiting an intermediate bend intermediate their distal and proximate ends which bring the tissue contacting distal ends of said legs toward each other, and a notch or groove, located in the applier contacting surface of each intermediate leg bend, each notch or groove extending generally normal to said longitudinal dimension of each leg, wherein said notches or grooves promote a tendency of said legs to straighten to a substantially gapless condition upon closure,
  wherein each of said notches or grooves redistribute the balance of compressive and tensile forces of the metal at each of said intermediate bends that would otherwise be present in the absence of said notches or grooves, and
  wherein each of said legs exhibits an applier contacting surface and an opposing tissue contacting surface, said surfaces being joined by opposite sidewall surfaces, said notches or grooves being located in said applier contacting surfaces, and further comprising a pair of fillets located respectively at the jointures of said sidewalls and said applier contacting surface at the hinge region of said clip, and a hinge recess located in the tissue contacting surface at said hinge region.

2. The metallic surgical hemostatic clip of claim 1, wherein said fillets extend generally parallel to said longitudinal dimension of said legs.

3. A surgical hemostatic clip comprising first and second legs having applier contacting sides and tissue contacting sides which oppose each other when the clip is closed, said legs having distal ends and being joined at their proximal ends at a hinge location, said hinge location having a V-shaped depression in said tissue contacting sides of said legs to promote maximal closure of the clip, the apex of said V-shaped depression being generally aligned with the proximal ends of said legs, and the sides of said depression extending substantially linearly outward from said apex of said depression to the surfaces of said tissue contacting sides of said legs, wherein said tissue contacting sides of said legs exhibit longitudinal grooves extending generally parallel to the longitudinal axes of said legs, said grooves intersecting the sides of said V-shaped depression in the vicinity of said hinge location, and wherein said longitudinal grooves terminate before their extension to the distal ends of said legs.

* * * * *